US009791688B2

(12) United States Patent
Hofer

(10) Patent No.: US 9,791,688 B2
(45) Date of Patent: Oct. 17, 2017

(54) ENDOSCOPE WITH TWO OPTICAL BEAM PATHS WITH SWITCHABLE MIRROR SURFACES

(75) Inventor: Axel Hofer, Endingen (DE)

(73) Assignee: Schölly Fiberoptic GmbH, Denzlingen (DE)

( * ) Notice: Subject to any disclaimer, the term of this patent is extended or adjusted under 35 U.S.C. 154(b) by 616 days.

(21) Appl. No.: 14/354,348

(22) PCT Filed: Aug. 18, 2012

(86) PCT No.: PCT/EP2012/003522
§ 371 (c)(1),
(2), (4) Date: Apr. 25, 2014

(87) PCT Pub. No.: WO2013/060401
PCT Pub. Date: May 2, 2013

(65) Prior Publication Data
US 2014/0293415 A1  Oct. 2, 2014

(30) Foreign Application Priority Data

Oct. 28, 2011  (DE) .................. 10 2011 117 389

(51) Int. Cl.
*A61B 1/00* (2006.01)
*G02B 23/24* (2006.01)
*G02B 26/02* (2006.01)
*A61B 1/04* (2006.01)

(52) U.S. Cl.
CPC ...... *G02B 23/2415* (2013.01); *A61B 1/00193* (2013.01); *G02B 26/02* (2013.01); *A61B 1/00181* (2013.01); *A61B 1/04* (2013.01)

(58) Field of Classification Search
CPC ............ A61B 1/00193; A61B 1/00181; A61B 1/00179; G02B 23/2415; G02B 26/02
See application file for complete search history.

(56) References Cited

U.S. PATENT DOCUMENTS

| 3,156,825 | A | * | 11/1964 | Lines | ........................ | H01P 5/16 |
|  |  |  |  |  |  | 333/13 |
| 3,291,554 | A | * | 12/1966 | Price | ...................... | G02B 26/02 |
|  |  |  |  |  |  | 359/222.1 |
| 3,614,211 | A | * | 10/1971 | Letter | ...................... | G03B 9/08 |
|  |  |  |  |  |  | 359/222.1 |
| 4,322,979 | A | * | 4/1982 | Fromm | ................. | G01L 9/0077 |
|  |  |  |  |  |  | 359/222.1 |
| 4,485,405 | A | * | 11/1984 | Bailey | .................. | H04N 5/2353 |
|  |  |  |  |  |  | 348/230.1 |
| 4,796,982 | A | * | 1/1989 | Kitabatake | .............. | G02F 1/315 |
|  |  |  |  |  |  | 359/318 |

(Continued)

FOREIGN PATENT DOCUMENTS

| WO | 2010047463 | 4/2010 |
| WO | 2010127827 | 11/2010 |

*Primary Examiner* — John P Leubecker
(74) *Attorney, Agent, or Firm* — Volpe and Koenig, P.C.

(57) ABSTRACT

In an endoscope (1), two optical paths (3, 4) for stereoscopic vision are formed, wherein each optical path (3, 4) is lead from the inside to an interface (16, 19) with an optically more dense material (14) in relation to the surroundings (13) at a point of incidence (22, 25), wherein each optical path (3, 4) can be opened and interrupted by modifying the reflection behavior at the respective point of incidence (22, 25).

10 Claims, 2 Drawing Sheets

(56) References Cited

U.S. PATENT DOCUMENTS

| | | | |
|---|---|---|---|
| 4,862,873 A * | 9/1989 | Yajima | A61B 1/00193 348/45 |
| 4,924,853 A * | 5/1990 | Jones, Jr. | A61B 1/00193 348/65 |
| 5,262,838 A * | 11/1993 | Tocher | G01C 3/04 356/16 |
| 5,944,655 A * | 8/1999 | Becker | G02B 23/2415 600/111 |
| 5,964,696 A * | 10/1999 | Mihalca | A61B 1/00193 348/45 |
| 6,377,383 B1 * | 4/2002 | Whitehead | B29C 59/16 359/222.1 |
| 7,405,877 B1 * | 7/2008 | Schechterman | A61B 1/00096 359/462 |
| 2008/0191127 A1 * | 8/2008 | Fine | H04N 5/2254 250/235 |
| 2010/0328748 A1 * | 12/2010 | Richardson | G02B 26/0883 359/222.1 |
| 2012/0127567 A1 | 5/2012 | Schouwink et al. | |

\* cited by examiner

ENDOSCOPE WITH TWO OPTICAL BEAM PATHS WITH SWITCHABLE MIRROR SURFACES

BACKGROUND

The invention relates to an endoscope having two optical beam paths adapted for stereoscopic viewing, wherein each beam path is guided in a section in an associated optical element made of an optically transmissive material and touches an interface of the material at a point of incidence from the inside.

Such endoscopes for stereoscopic viewing are known and have proven themselves, wherein the optical beam paths are assigned to a left-hand and a right-hand viewing field for obtaining images having image depth information (3-D images).

In order to avoid light losses, if possible, in the endoscope, optical elements are frequently used which enable a reflection of the beam path without mirrors. These optical elements are made of an optically transmissive material in which the beam path is guided, wherein the beam path touches an interface of the material from the inside at a point of incidence, that is to say at the transition from the optically more dense medium to the optically less dense medium such that the beam undergoes total internal reflection. This has the advantage that the reflection behavior at the point of incidence is improved with respect to a conventional mirror. The reflection behavior can be described for example by a reflection coefficient, in particular in relation to a direction of incidence defined by the respective beam path.

In endoscopes for stereoscopic viewing, it has become customary to arrange an image recording chip in the distal region, which records images from the two optical beam paths in alternation.

In this respect it has been suggested to provide a mechanically adjustable mirror which is variable between two adjustment positions and directs the beam paths in alternation onto the image recording chip. This necessitates a great pivot path of the mirror and a complicated suspension of the mirror.

SUMMARY

The invention is based on the object of increasing the mechanical robustness of an endoscope for stereoscopic viewing.

To achieve this object, provision is made according to the invention in an endoscope of the type described in the introductory part for in each case one switchable mirror surface to be formed at the points of incidence of the beam paths, with which the reflection behavior is variable at the respective point of incidence. Advantageous here is that an alternating guidance of the beam paths onto an image recording chip is possible without having to actuate mechanically pivotable mirrors. This simplifies the design and increases the mechanical robustness of the overall system. The switchable mirror surface preferably comprises a structure which is formed on the outside, that is to say outside the material, at the interface.

The structure can be adapted such that the mirror surface is switchable between a reflective and a non-reflective state.

In one embodiment of the invention, provision may be made for the switchable mirror surface to be adapted for changing the refractive index in a surrounding area of the point of incidence outside the material. Advantageous here is that a critical angle of the total internal reflection is easily variable at the point of incidence such that the interface is switchable between a state in which the beam path undergoes total internal reflection and a state in which the interface is transmissive and substantially does not reflect. After all, the critical angle of the total internal reflection is determined by the ratio of the refractive indices on both sides of the interface.

In one embodiment of the invention, provision may be made for the switchable mirror surfaces to be adapted to be switchable in each case between a reflective switching position and a non-reflective or absorptive switching position. Advantageous here is that only short or even no switching paths at all are necessary to switch between the switching positions, since the switching position correlates non-linearly with the respectively attained beam guidance. It is thus possible with small switching processes to achieve a qualitative change of the beam paths.

In one embodiment of the invention, provision may be made for the switchable mirror surfaces in each case to have a switching element which is switchable between a first switching position, in which the switching element rests areally on the interface at the point of incidence, and a second switching position, in which the switching element is spaced apart from the interface. This represents a particularly simple method for influencing the occurrence of total internal reflection at the interface. The refractive index of the switching element is preferably different from the refractive index of the surrounding area (for example air or vacuum or a protective gas or a liquid), or the switching element is non-transmissive to light. The advantage here is that the switching element can be used to displace a medium arranged on the outside at the interface. The refractive index is thus variable in steps by replacing the medium with the switching element. The switching elements can be formed to be separate from one another or be coupled to one another or be connected in one piece.

In one embodiment of the invention, provision may be made for the interface at the point of incidence to be formed as a smooth surface which has total internal reflection. For the interface, a critical angle for the total internal reflection is thus defined from which point total internal reflection occurs. The smooth surface may also be made reflective.

Provision may for example be made for the beam path in the material to be guided onto the point of incidence such that the beam path undergoes total internal reflection in a first switching position and the beam path does not undergo total internal reflection or is even absorbed in a further switching position of the switchable mirror surface.

In one embodiment of the invention, provision may be made for the interface at the point of incidence to be formed as a rough surface which prevents total internal reflection. The interface may in this case be formed with a roughness which effects a diffuse exit of the beam path from the material into the surrounding air or the surrounding medium. If the unevennesses of the roughness are filled with a substance of a suitable refractive index, it is possible to achieve that the beam path is reflected at the changed interface.

In one embodiment of the invention, provision may be made for the switching element to be adapted to be electrically switchable. Advantageous here is that the actuation of the switchable mirror surface and the supply of the energy necessary for switching are realizable particularly easily.

Provision may be alternatively made for the switching element to be adapted to be pneumatically or hydraulically switchable. Advantageous here is that electrical supplies for the switchable mirror surfaces are omittable.

In order to realize a particularly simple, compact construction, provision may be made for the optical elements of the beam paths to be connected to one another in one piece.

In order to be able to mechanically decouple the optical elements, provision may be made for them to be formed to be separate.

In order to guide the two beam paths in alternation onto an image recording chip used in common, provision may be made for each beam path in a reflective switching position of the associated switchable mirror surface to be guided onto an image recording chip used in common by both beam paths. By way of example, the reflective switching position at the switchable mirror can be that in which total internal reflection for the beam path occurs at the point of incidence.

Provision may also be made for each beam path in a non-reflective or absorptive switching position of the associated switchable mirror surface to be guided onto a light trap. Advantageous here is that the two beam paths do not disturb one another but are capturable separately, for example in alternation, on an image recording chip.

For stereoscopic viewing, provision may be made for a switching logic to be present with which the switchable mirror surfaces are switchable at the same time or in a coupled fashion, preferably coupled in opposition. Here, the switching logic can be adapted such that it switches the switching mirrors in alternation. Advantageous here is that a coupling between the switchable mirror surfaces which effects simultaneous switching of the switchable mirror surfaces is set up in a simple manner, such that always exactly one beam path is directed onto an image recording chip or a shared optical channel. The respectively other beam path can in this case be respectively deflected or absorbed such that light carried by it does not disturb.

BRIEF DESCRIPTION OF THE DRAWINGS

The invention will now be explained in more detail with reference to exemplary embodiments, without being restricted to these exemplary embodiments. Further exemplary embodiments result from a combination of individual or several features of the claims among one another and/or with individual or several features of the exemplary embodiments.

In strongly simplified, schematic illustration for explanation of the inventive principle.

DETAILED DESCRIPTION OF THE PREFERRED EMBODIMENTS

Figure 1:
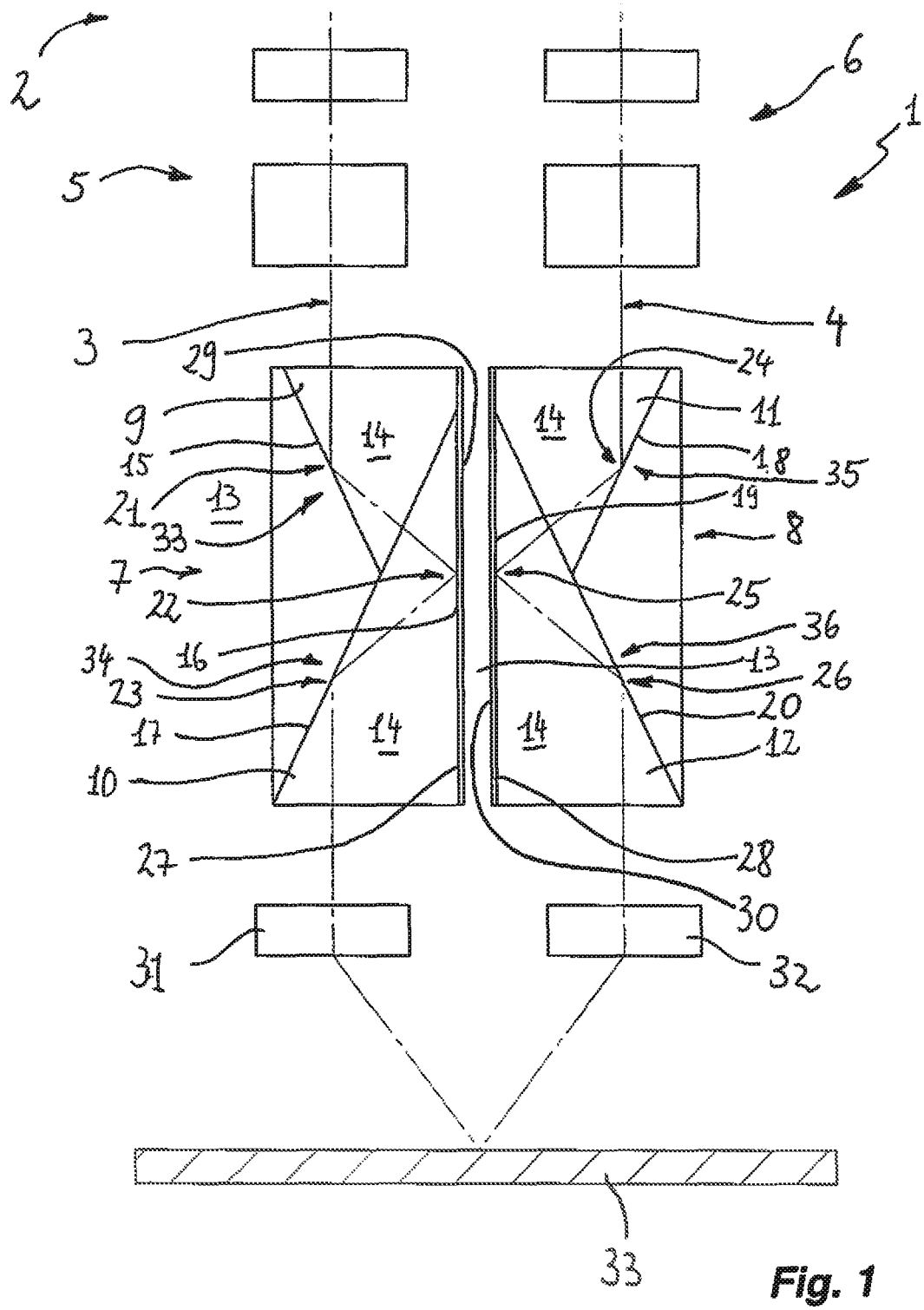
FIG. 1 shows an endoscope according to the invention with mutually separate optical elements.

FIG. 1 shows, in a strongly simplified illustration, an endoscope according to the invention which is designated throughout with 1.

In this endoscope 1, those components which directly cooperate to implement the invention are illustrated, while other components which are known per se and are not necessary to complete a usable endoscope have been omitted for simplification of the illustration.

The components shown in FIG. 1 of the endoscope 1 can be arranged for example in a distal region at the distal end 2 of a tubular housing for forming a rigid endoscope. The components can also be arranged at the distal end 2 in a housing in the manner of a flexible tube of a flexible endoscope 1.

The distal end 2 is located at the top in the illustration according to FIG. 1.

Two beam paths 3, 4 are arranged at the endoscope 1, with which images at the distal end 2 are capturable.

The beam paths 3, 4 are adapted for stereoscopic viewing, wherein the beam path 3 corresponds to a left-hand viewing field and the beam path 4 corresponds to a right-hand viewing field.

Each of the beam paths 3, 4 is guided through an objective assembly 5, 6 onto a prism assembly 7, 8. The objective assemblies 5, 6 can be configured to be separate from one another or in pairs—in each case a left-hand and a right-hand element—in one piece at a shared lens body. The one-piece embodiment of the elements of the objective assembly is easier to install.

The prism assemblies 7, 8 have optical elements 9, 10, 11, 12, which consist of an optically transmissive material 14 having a refractive index which is greater than the refractive index of the surrounding area 13, for example made of glass.

Since the refractive index of the material 14 is greater than the refractive index of the surrounding area 13, which can for example be air or another gas or vacuum, total internal reflection occurs starting from a specific angle of incidence at the interfaces 15, 16, 17, 18, 19, 20 of the material 14 of the optical elements 9, 10, 11, 12.

This is used for beam guidance of the beam paths 3, 4 by guiding the beam paths 3, 4 through the optically transmissive material 14 of the optical elements 9, 10, 11, 12 such that they touch the interfaces 15, 16, 17, 18, 19, 20 at a point of incidence 21, 22, 23, 24, 25, 26 from the inside. The light in the beam paths 3 and 4 cannot exit at the points of incidence 21, 22, 23, 24, 25, 26 into the optically thinner medium, the surrounding area 13, but undergoes total internal reflection in the material 14.

In the surrounding area of the points of incidence 22, 25, in each case a switchable mirror surface 27, 28 is formed at the interfaces 16, 19.

The switchable mirror surface 27 is here associated with the left-hand beam path 3 and the switchable mirror surface 28 is associated with the right-hand beam path 4. One switchable mirror surface 27, 28 is thus associated with each beam path 3, 4.

The switchable mirror surfaces 27, 28 can be used to vary the reflection behavior at the point of incidence 22 and 25, respectively.

It is thus possible with the switchable mirror surfaces 27, 28 to control whether or not the beam paths 3, 4 are reflected at the points of incidence 22, 25. FIG. 1 shows for both beam paths 3, 4 the case that the beam paths 3, 4 are reflected at the points of incidence 22, 25. However, this case does not occur during use. Rather, only one of the beam paths 3, 4 at a time is reflected at the respective point of incidence 22, 25, while the other beam path 3, 4 is not reflected.

The change in the reflection behavior is effected by changing the refractive index in the surrounding area 13 of the point of incidence 22, 25 outside the material 14.

This takes place using a switching element 29, 30.

The switching element 29, for example a thin film, can be switched between a first switching position and a second switching position.

In the first position, the switching element 29 rests areally on the interface 16 on the outside. With a suitable selection of the refractive index of the switching element 29, this brings about that no more total internal reflection occurs for the incoming light beam along the beam path 3. The switching element 29 displaces the air of the surrounding area 13 of the interface 16 and thus changes the refractive index outside and near the interface 16. As a result, the critical angle of the total internal reflection changes or even disappears completely.

The beam path 3 is thus interrupted at the site of the point of incidence 22 in the first switching position. This is thus the absorptive or non-reflective switching position of the switchable mirror 27.

In the second switching position, the switching element 29 is arranged to be spaced apart from the interface 16 such that total internal reflection occurs at the interface 16 which is formed as a smooth surface. After all, the surrounding area 13 of the interface 16, that is to say the space between the interface 16 and the switching element 29, is now filled with air which has a lower refractive index than the material 14. In the second switching position of the switching element 29, the light trapped via the objective assembly 5 is thus guided along the beam path 3, as shown in FIG. 1, beyond the point of incidence 22. This is thus the reflective switching position of the switchable mirror 27.

Similarly, a switching element 30 of the switchable mirror surface 28 is formed at the optical element 12, which switching element 30 is likewise switchable between a first, absorptive switching position, in which the switching element 30 rests areally on the interface 28, and a second, reflective switching position, in which the switching element 30 is spaced apart from the interface 28.

Due to a change between the two switching positions, the beam path 4 can thus be enabled or be interrupted at the point of incidence 25.

The switching elements 29, 30 can be actuable for example electrically via piezo elements (not illustrated in more detail) and be switchable between the two switching positions. The switching elements 29, 30 can be formed to be separate from one another or be in one piece or be connected with one another indirectly. On account of this connection, it is possible to achieve in a simple manner that a change between the two switching positions is effected at the switchable mirror surface 27 at the same time as an inverse or opposite change between the two switching positions at the switchable mirror surface 28.

The switching elements 29, 30 can also be adapted to be pneumatically or hydraulically switchable.

Controlling the beam path 3, 4 via a reflection behavior at the transition from the material 14 to the surrounding area 13 at the point of incidence 22, 25 has the advantage that the switching elements 29, 30 must in each case cover only short switching paths in order to interrupt or enable the beam paths 3, 4.

The interfaces 16, 19 can be formed in a further exemplary embodiment alternatively as rough surfaces. In this case, the light which is incident via the objective assemblies 5, 6 along the beam paths 3, 4 at the points of incidence 22, 25 is emitted diffusely into the surrounding area 13 if the respective switching element 29, 30 does not areally touch the interface 16, 19, but is arranged at a distance therefrom.

If in this case the switching element 29, 30 is pressed against the interface 16, 19, with suitable selection of the material of the switching element 29, 30, a mirror surface forms at which the beam path 3, 4 is reflected specularly in the point of incidence 22, 25, as shown in FIG. 1, and continued.

In this case, the switching position in which the switching element 29 (or 30) rests areally on the interface 16 (or 19) is therefore the reflective switching position, while the switching position in which the switching element 29 (or 30) is arranged to be spaced apart from the interface 16 (or 19) represents the absorptive switching position.

To illustrate the beam guidance, FIG. 1 shows the beam paths 3, 4 for the reflective switching position of the switchable mirror surfaces 27, 28.

In the reflective switching position illustrated in FIG. 1, the beam path 3 and the beam path 4 are guided via a lens 31 and 32 onto an image recording chip 33 used in common by both beam paths 3, 4. The lenses 31, 32 can be configured to be separate from one another or in one piece at a shared lens body. The one-piece embodiment has the advantage of simpler installation.

In the respective absorptive switching position of the switchable mirror surfaces 27, 28, the points of incidence 22, 25 form light traps at which the beam paths 3, 4 terminate or are deflected to the outside into the surrounding area 13.

Depending on the switching position of the switchable mirror surfaces 27, 28, the image recording chip 33 thus either records a left-hand image, incident via the objective assembly 5, or a right-hand image, incident via the objective assembly 6.

These recorded images are subsequently electronically or digitally processed in a manner known per se in order to digitally or electronically provide a stereoscopic image.

In order that the image recording chip 33 in each case records only an image from the beam path 3 or from the beam path 4, a switching logic is provided (not illustrated in more detail) with which the switchable mirror surfaces 27, 28 are switchable in opposition at the same time or coupled. Switching in opposition means in this case that a change from the reflective switching position to the non-reflective switching position at a switchable mirror surface is accompanied by an opposite change from the non-reflective switching position to the reflective switching position at the other switchable mirror surface.

Figure 2:
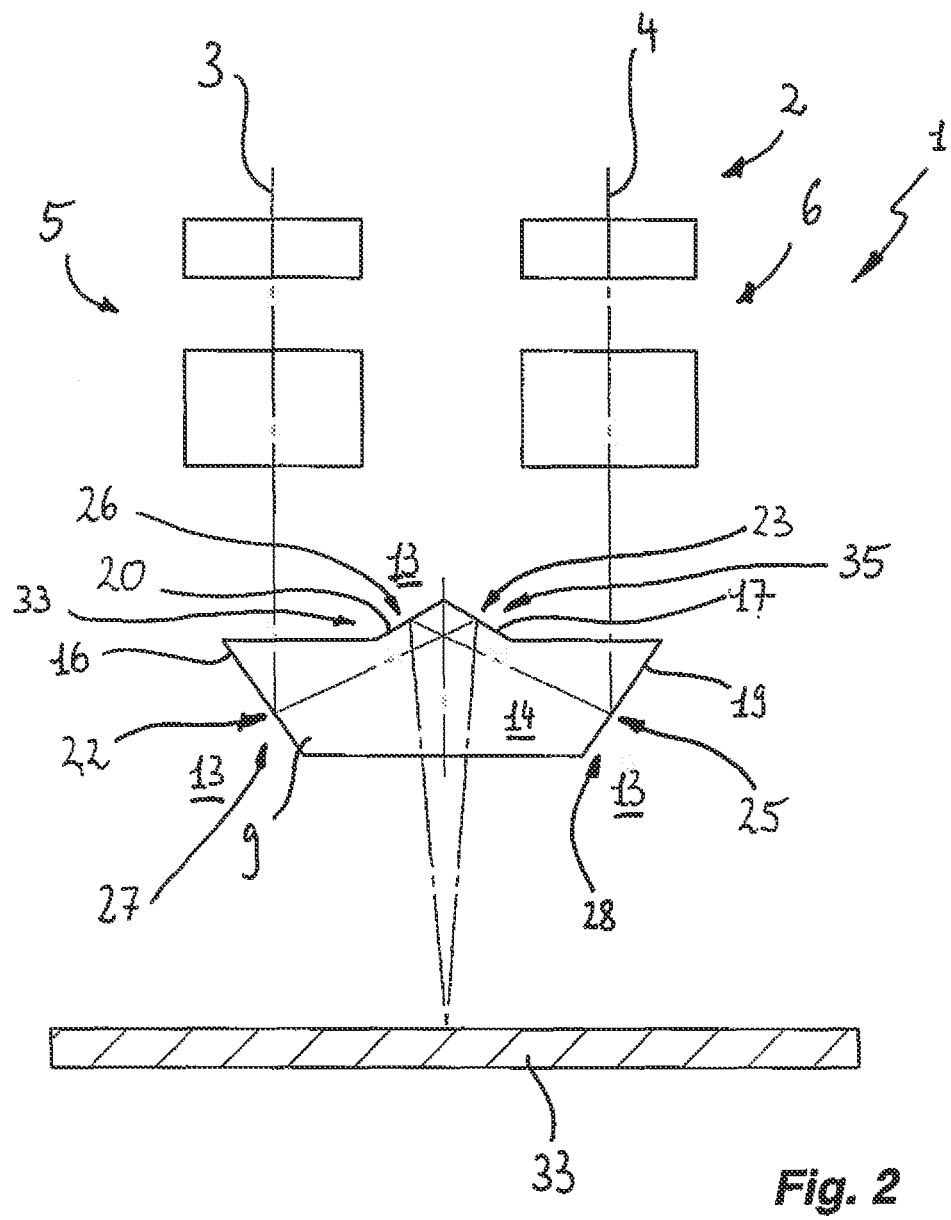
FIG. 2 shows a further endoscope according to the invention having optical elements which are connected to one another in one piece.

FIG. 2 shows a further endoscope 1 according to the invention in a strongly simplified principle illustration, in which again only the components which cooperate directly for the realization of the principle according to the invention are shown. The remaining components have been omitted for simplicity.

In FIG. 2, components which are identical or have identical action functionally or structurally with respect to the embodiment according to FIG. 1 have the same reference signs and are not described again separately.

In the exemplary embodiment according to FIG. 2, the left-hand beam path 3 is guided via a left-hand objective assembly 5 into the material 14 of the one-piece optical element 9.

The beam path 3 undergoes total internal reflection in the material 14 at the points of incidence 22 and 26 at the interfaces 16 and 20. Subsequently, the beam path 3 exits the optical element 9 and is incident on the image recording chip 33.

A switchable mirror surface 27 is again formed at the interface 16, which mirror surface 27 can interrupt or enable the beam path 3 at the point of incidence 22. The switchable mirror surface 27 can be configured as illustrated for example in FIG. 1 and described in relation to FIG. 1.

In the interrupting or absorptive or non-reflective switching position of the switchable mirror surface 27, thus no light arrives on the image recording chip 33 via the beam path 3 and the objective assembly 5, whereas in the reflective or enabling switching position of the switchable mirror surface 27 the light, which is trapped by the objective assembly 5, is guided onto the image recording chip 33.

The right-hand beam path 4 is likewise guided via the right-hand objective assembly 6 into the optical element 9 and undergoes total internal reflection in the material 14 of the optical element 9 at the points of incidence 25, 26 at the interfaces 19, 20.

A switchable mirror surface 28, with which the reflection behavior at the point of incidence 25 is variable, is formed at the interface 19 on the outside at the optical element 9.

The switchable mirror surface 28 is switchable between two switching positions, wherein in a reflective switching position, the illustrated beam path 4 is formed, in which reflection occurs at the point of incidence 25, whereas in the absorptive or non-reflective switching position, the beam path 4 is interrupted at the point of incidence 25 and is deflected into a light trap (not illustrated in more detail) outside the optical element 9. The switchable mirror surface 28 is configured to be identical functionally and structurally to the switchable mirror surface 27.

Either the beam path 3 or the beam path 4 can thus be guided onto the image recording chip 33 with alternating actuation or switching of the switchable mirror surface 27, 28.

The switchable mirror surfaces 27, 28 can have, for example, a layer made of a material whose refractive index is variable electrically or in another fashion. Alternatively or additionally, the switchable mirror surfaces 27, 28 can in each case contain switching elements (not illustrated in more detail), which, similarly to the exemplary embodiment of FIG. 1, can be brought into touching contact with the interfaces 16, 19 in order to enable or prevent reflection at the points of incidence 22 and 25.

The switchable mirror surfaces 27, 28 can, alternatively or additionally, be arranged in FIGS. 1 and 2 also at one or more of the remaining interfaces 15, 16, 17, 18, 19, 20. Additional or alternative mirror surfaces 33, 34, 35, 36 are formed in this manner. These mirror surfaces 33, 34, 35, 36 are configured to be identical functionally and structurally to the already described switchable mirror surfaces 27, 28.

FIG. 2 also shows that the optical elements of the beam paths 3, 4, at which the switchable mirror surfaces are formed, are made such that they are connected in one piece as a common optical element 9. The optical element 9 can thus be installed in a few work steps.

The figures finally show that the beam paths 3, 4 are guided due to the alignment of the objective assemblies 5, 6 and of the interfaces 15, 16, 17, 18, 19, 20 in a section in the material 14 of the optical elements 9, 10, 11, 12 of the prism assemblies 7, 8.

In further exemplary embodiments, some or all those interfaces 15, 17, 18, 20 that carry no switchable mirror surface 27, 28, 33, 34, 35, 36, are provided with an outside coating, which reflects the beam path 3, 4. This can be the case for example if the angle of incidence at the respective interface 15, 17, 18, 20 is unfavorable for total internal reflection.

It is proposed for the endoscope 1 to form two beam paths 3, 4 for stereoscopic viewing, wherein each beam path 3, 4 is guided to a point of incidence 22, 25 from the inside at an interface 16, 19 of a material 14 which is optically more dense with respect to the surrounding area 13, wherein each of the beam paths 3, 4 is enableable and interruptible by changing the reflection behavior at the respective point of incidence 22, 25.

The invention claimed is:

1. An endoscope (1) comprising two optical beam paths (3, 4) adapted for stereoscopic viewing, an associated optical element (9, 10, 11, 12) for each of the beam paths made of an optically transmissive material (14) that guides each of the beam paths (3, 4) in a section to an interface (15, 16, 17, 18, 19, 20) of the optically transmissive material (14) at a reflective point of incidence (21, 22, 23, 24, 25, 26) from an inside, each of the associated optical elements having one associated switchable mirror surface (27, 28, 33, 34, 35, 36) at the points of incidence (21, 22, 23, 24, 25, 26) of the beam paths (3, 4) with which a reflection behavior is variable at the respective point of incidence (21, 22, 23, 24, 25, 26), wherein the switchable mirror surfaces each have a switching element that is switchable between a first switching position, in which the switching element is arranged areally on the interface (15, 16, 17, 18, 19, 20) at the point of incidence (21,22,23,24,25,26), and a second switching position, in which the switching element (29,30) is spaced apart from the interface (15, 16, 17, 18, 19, 20), the switching elements are integrally or indirectly physically connected to one another, so that a mechanical alternation between first and second ones of the switching positions of the switching element on a first of the switchable mirror surfaces (27) is effected at a same time with a reversed change between the two switching positions of the switching element on a second of the switchable mirror surfaces (28).

2. The endoscope (1) as claimed in claim 1, wherein the switchable mirror surfaces (27, 28, 33, 34, 35, 36) are adapted for changing a refractive index in a surrounding area (13) of the point of incidence (21, 22, 23, 24, 25, 26) outside the optically transmissive material (14).

3. The endoscope (1) as claimed in claim 1, wherein the interface (15, 16, 17, 18, 19, 20) at the point of incidence (21, 22, 23, 24, 25, 26) is formed as a smooth surface which provides total internal reflection or is made reflective.

4. The endoscope (1) as claimed in claim 1, wherein the switching element (29, 30) is electrically, pneumatically or hydraulically switchable.

5. The endoscope (1) as claimed in claim 1, wherein each of the beam paths (3, 4) in a reflective switching position of the associated switchable mirror surface (27, 28, 33, 34, 35, 36) is guided onto an image recording chip (33) used in common by both of the beam paths (3, 4).

6. The endoscope (1) as claimed in claim 1, wherein each of the beam paths (3, 4) in a non-reflective or absorptive switching position of the associated switchable mirror surface (27, 28, 33, 34, 35, 36) is guided onto a light trap.

7. The endoscope as claimed in claim 1, further comprising a switching logic with which the switchable mirror surfaces (27, 28, 33, 34, 35, 36) are switchable.

8. The endoscope as claimed in claim 7, wherein the switchable mirror surfaces are switchable in coupled opposition.

9. The endoscope as claim in claim 1, wherein the switchable mirror surfaces (27, 28, 33, 34, 35, 36) are adapted to be switchable between a reflective switching position and a non-reflective or absorptive switching position.

10. An endoscope (1) comprising two optical beam paths (3, 4) adapted for stereoscopic viewing, an optical element (9) for the beam paths made of an optically transmissive material (14) that guides each of the beam paths (3, 4) in a section to an interface (16, 17, 19, 20) of the optically transmissive material (14) at a reflective point of incidence (22, 23, 25, 26) from an inside, the optical element having switchable mirror surfaces (27, 28, 33, 35) at the points of incidence (22, 23, 25, 26) of the beam paths (3, 4) with which a reflection behavior is variable at the respective point of incidence (22, 23, 25, 26), wherein the switchable mirror surfaces each have a switching element that switches the switchable mirror surfaces between a first switching position, in which the switching element is arranged areally on the interface (16, 17, 19, 20) at the point of incidence (22,23,25,26), and a second switching position, in which the switching element (29,30) is spaced apart from the interface (16, 17, 19, 20), the switching elements are controlled so that an alternation between first and second ones of the switching positions of the switching element on a first of the switchable mirror surfaces (27) is effected at a same time with a reversed change between the two switching positions of the switching element on a second of the switchable mirror surfaces (28), and the optical element that carries the beam paths (3, 4) is formed integrally in one piece.

\* \* \* \* \*